(12) United States Patent
Moeller et al.

(10) Patent No.: US 7,554,723 B2
(45) Date of Patent: Jun. 30, 2009

(54) OPHTHALMOLOGIC SURGICAL MICROSCOPE HAVING FOCUS OFFSET

(75) Inventors: Gerhard Moeller, Göttingen (DE); Peter Reimer, Ellwangen (DE); Peter Andrews, Oberkochen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 208 days.

(21) Appl. No.: 11/372,209

(22) Filed: Mar. 10, 2006

(65) Prior Publication Data

US 2006/0203330 A1 Sep. 14, 2006

(30) Foreign Application Priority Data

Mar. 11, 2005 (DE) ................. 10 2005 011 781

(51) Int. Cl.
*G02B 21/00* (2006.01)
(52) U.S. Cl. .................. 359/383; 358/368; 358/381
(58) Field of Classification Search .......... 359/368–390
See application file for complete search history.

(56) References Cited

U.S. PATENT DOCUMENTS

| 4,958,920 A | 9/1990 | Jorgens et al. |
|---|---|---|
| 5,867,308 A | 2/1999 | Pensel et al. |
| 6,005,710 A | 12/1999 | Pensel et al. |
| 6,212,006 B1 | 4/2001 | Reiner |
| 6,542,293 B2 | 4/2003 | Yahiro |
| 7,034,883 B1* | 4/2006 | Rosenqvist ............ 348/345 |
| 7,071,451 B2* | 7/2006 | Ishikawa et al. ........ 250/201.4 |
| 2002/0191280 A1* | 12/2002 | Horiguchi et al. .......... 359/383 |
| 2003/0165012 A1 | 9/2003 | Straehle et al. |
| 2005/0068614 A1* | 3/2005 | Yoneyama et al. ........ 359/368 |

FOREIGN PATENT DOCUMENTS

| DE | 35 39 009 | 5/1987 |
|---|---|---|
| DE | 201 11 006 U | 6/2001 |
| DE | 103 12 682 | 2/2003 |

\* cited by examiner

*Primary Examiner*—Thong Nguyen
(74) *Attorney, Agent, or Firm*—Walter Ottesen

(57) ABSTRACT

A microscope arrangement (200) is for viewing an object or an intermediate image, which is generated by an object, especially in microsurgery. The microscope arrangement (200) includes an objective arrangement (201) having an object plane (209) for arranging the object or intermediate image (210) to be viewed. The microscope arrangement has a focus offset adjusting unit (260) which outputs a focusing offset signal in order to defocus in a defined manner the objective arrangement relative to a focusing state.

10 Claims, 7 Drawing Sheets

OPHTHALMOLOGIC SURGICAL MICROSCOPE HAVING FOCUS OFFSET

CROSS REFERENCE TO RELATED APPLICATION

This application claims priority of German patent application no. 10 2005 011 781.3, filed Mar. 11, 2005, the entire content of which is incorporated herein by reference.

FIELD OF THE INVENTION

The invention relates to an ophthalmologic surgical microscope for microsurgery for viewing an object or an intermediate image, which is generated by the object, wherein an objective arrangement is provided which can be adjusted to focus on an object plane in which an object or intermediate image is disposed which is intended to be viewed.

BACKGROUND OF THE INVENTION

An ophthalmologic surgical microscope of the kind referred to above is known from German patent publication DE 35 39 009 A1. There, an ophthalmologic surgical microscope is described which is equipped with an ancillary module which includes an ophthalmoscopic magnifier and a system for beam transposition and image reversion. The surgical microscope has a microscope main objective system having an intercept distance which can be adjusted. Accordingly, it is possible with the surgical microscope to sharply adjust the image of an intermediate image, which is generated by the ophthalmoscopic magnifier, or the image of an object region without it being necessary to move the surgical microscope or that additional optical elements are needed which have to be switched into the viewing beam path when the ancillary module is not in the viewing beam path.

Surgery on the human eye, for example, cataract surgery, is, as a rule, carried out utilizing a surgical microscope. The human eye is a spatially expanded organ which is accessible to a surgeon only from the side of the cornea. During the course of surgery, there is therefore the need for a surgeon to view sharply different planes in the eye.

The depth of field ST of a surgical microscope is dependent upon an adjusted magnification $\beta$ and can be estimated as follows:

$$ST \approx \frac{0.5\lambda}{NA^2} + \frac{0.34 \text{ mm}}{\beta NA},$$

wherein NA is the numerical aperture of the viewing beam path of the main objective of the surgical microscope and $\lambda$ is the wavelength of the light with which an area of surgery is illuminated. For conventional magnifications of 5 to 30 times, there thereby results a depth of field which is less than the spatial expanse of the eye from the cornea to the ocular fundus. This condition has the consequence for the surgeon that the surgical microscope during the course of a surgical procedure must be refocused in correspondence to the plane in the eye at which surgery is just then taking place.

The physiological structures in an eye are substantially transparent. This makes it difficult for a surgeon to sharply adjust the surgical microscope onto different planes in the eye whereat surgery is taking place.

U.S. Pat. No. 6,212,006 describes a surgical microscope designed for eye surgery. The surgical microscope has a base body which is held on a carrier arm of a surgical microscope stand above the head of a patient to be operated upon. The surgical microscope has a microscope main objective via which a surgeon can view the patient eye to be operated upon via a stereoscopic viewing tube. The surgical microscope is equipped with an ophthalmoscopic magnifier which can be pivoted into or out of the viewing beam path. Because of the refractive power of cornea and lens in a human eye, an ophthalmoscopic magnifier arranged close in front of the eye must be used in order to be able to examine the ocular fundus with the surgical microscope. If, on the other hand, structures in the area of the cornea and lens of an eye are to be magnified with the surgical microscope, then the ophthalmoscopic magnifier is removed from the viewing beam path. In lieu of an ophthalmoscopic magnifier, so-called contact lenses are also used in eye surgery which are optical elements which are placed on the patient eye to be examined and which have a positive refractive power which cancels the refractive power of the cornea.

Autofocus systems in surgical microscopes are known. A surgical microscope having an autofocusing unit is described in German patent publication 201 11 006 U1. The autofocusing unit includes an image sensor on which the object region, which is examined by means of the surgical microscope, is imaged via a beam splitter prism having an autofocus beam path. An evaluation unit is assigned to the image sensor by means of which a contrast of an area of the image, which is detected by the image sensor, can be specified. The evaluation unit is connected via a control line to a drive for a displaceable lens in the microscope main objective system. The displaceable lens is always adjusted because of the signal from the evaluation unit so that the area of the image, which is detected by the image sensor, always has a maximum contrast.

United States patent application publication US 2004/0090667 A1 discloses a surgical microscope wherein a focusing state is determined on an image sensor from the offset of a scanning light beam which is scattered in the object region. In this way, it is possible even with low contrast of an object region to detect the focusing state of the surgical microscope.

U.S. Pat. Nos. 5,867,308 and 6,005,710 disclose a surgical microscope having an autofocusing system wherein the autofocusing system can be activated by means of an eye control.

The fault-free function of such an autofocus system has as a condition precedent that either structures are present in the object region which cause a contrast or that the scanning light beam in the object region is so scattered that an occurring scatter light image can be captured by an image sensor. However, if an organ, which is transparent over wide regions such as the human eye, is examined, the functioning of an autofocus system is not guaranteed in each case because, not in all levels of the eye are there structures which have a high contrast or scatter a scanning light beam.

SUMMARY OF THE INVENTION

It is an object of the invention to provide a viewing assist for carrying out surgical procedures on a human eye wherein the surgeon is enabled to view rapidly and sharply different planes or levels of the eye.

In the ophthalmologic surgical microscope of the invention, an autofocus system is provided with a component assembly which detects a focusing state of the objective arrangement and outputs a focusing adjusting signal for the objective arrangement. A focus offset adjusting unit is assigned to the autofocus system. This focus offset adjusting unit outputs a focus offset signal to adjust the objective arrangement by a predetermined focus offset starting from a first focusing state wherein the objective arrangement is focused on a first object plane to a second focusing state wherein the objective arrangement is focused onto a second object plane.

In this way, the ophthalmologic surgical microscope can be automatically focused onto an object plane or intermediate image plane which has only a slight contrast or slight scatter capacity for light.

In another embodiment of the invention, an input unit is assigned to the focus offset adjusting unit which makes it possible for an operator to select a desired value for an offset of the focus of the objective arrangement from a focusing state which the focus offset adjusting unit sets. In this way, the possibility is afforded to select section planes of a patient eye which are to be sharply viewed.

In a further embodiment of the invention, an ophthalmoscopic magnifier is provided which can be positioned selectively in the viewing beam path of the ophthalmologic surgical microscope or outside of the viewing beam path of the ophthalmologic microscope. Switching means are provided which activate the autofocus system when positioning the ophthalmoscopic magnifier in the viewing beam path.

In a further embodiment of the invention, an ophthalmoscopic magnifier is provided which can be positioned selectively in the viewing beam path of the ophthalmologic surgical microscope or outside of the viewing beam path of the ophthalmologic surgical microscope. Switching means are provided which activate the autofocusing system when positioning the ophthalmoscopic magnifier outside of the viewing beam path. In this way, a surgeon rapidly obtains sharp images from the anterior chamber and the ocular fundus during surgical procedures on the eye.

In a further embodiment of the invention, the switching means are coupled with: means for controlling an illuminating unit of the opthalmologic surgical microscope and/or with means for controlling the illumination in an operating room and/or with means for arranging an image reversion system in the viewing beam path of the ophthalmologic surgical microscope. In this way, when viewing the anterior chamber and ocular fundus, an image correct and laterally correct view of the just then examined object is made visible to a surgeon.

In a further embodiment of the invention, a stereoscopic viewing beam path is provided for the ophthalmologic surgical microscope. In this way, a spatial view of the object region is provided to the surgeon.

In a further embodiment of the invention, means for determining an image contrast are assigned to the component assembly which detects a focusing state of the objective arrangement and outputs a focusing actuating signal for the objective arrangement.

In a further embodiment of the invention, selection means are provided for an image zone whose contrast can be determined with the means for determining the image contrast. In this way, the surgeon can select structures on the eye whose image is selected for an autofocusing operation.

According to another feature of the invention, a focus offset adjusting unit is provided which outputs a focusing offset signal to an adjusting unit for the objective arrangement in order to focus the objective arrangement utilizing an adjustment by a predetermined focus offset starting from a first focusing state of the objective arrangement wherein the objective arrangement is focused on a first object plane to a second focusing state wherein the objective arrangement is focused on a second object plane. An input unit is assigned to the focus offset adjusting unit which enables an operator to input a desired value for a predetermined focus offset. In this way, it is possible during eye surgery to manually adjust the ophthalmologic surgical microscope onto the iris of a patient eye and to then automatically displace the focus plane of the arrangement into the interior of the patient eye.

Preferably, an ophthalmoscopic magnifier is provided for the ophthalmologic surgical microscope and can be selectively arranged in the viewing beam path and outside of the viewing beam path of the opthalmologic surgical microscope. In this case, it can be practical when a switch is provided which is activated when arranging the ophthalmoscopic magnifier in the viewing beam path and then triggering a focus offset signal of the focus offset adjusting unit to the displacing unit for the objective arrangement. Correspondingly, it can be provided that, for an arrangement of the ophthalmoscopic magnifier outside of the viewing beam path, the switch is also activated in order, in turn, to effect a focus offset signal of the focus offset adjusting unit to the displacing unit for the objective arrangement. When the focus offset signal of the focus offset adjusting unit adjusts a focus offset for the adjusting unit for the objective arrangement, which lies in the region of 1 mm to 80 mm, preferably at approximately 50 mm, it is achieved that with and without the ophthalmoscopic magnifier in the viewing beam path, a surgeon can always view a sharp image of different planes of a surgical area.

Preferably, if the microscope arrangement is operated in that first a desired focus plane of the objective arrangement is set and then, by actuating an operator-controlled unit, a focus offset of the objective arrangement is adjusted correspondingly to a pregiven value. This value for a specific focus offset can be adjusted in advance depending upon situation. It can be provided that the focus plane of the objective arrangement is automatically adjusted by means of an autofocus system.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
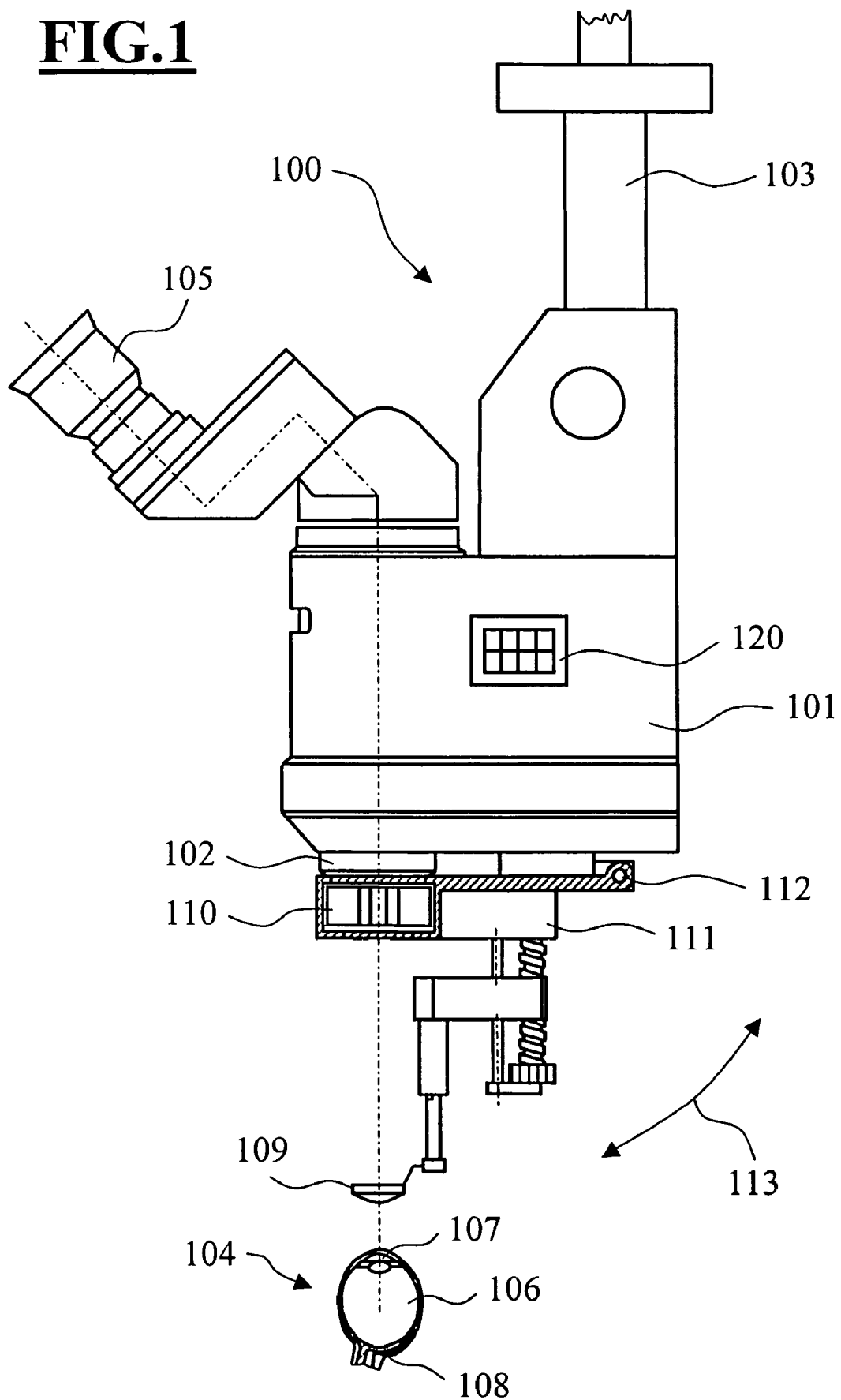
FIG. 1 is a side elevation view of an ophthalmologic or ophthalmic surgical microscope having an ophthalmoscopic magnifier.

In FIG. 1, an ophthalmic surgical microscope 100 is shown as a microscope arrangement for viewing an object in the form of a human eye. The ophthalmic surgical microscope 100 includes a surgical microscope base body 101 in which a microscope main objective system 102 with a zoom system is accommodated. The microscope main objective 102 is focusable by means of a drive. The surgical microscope base body 101 is held by a carrier arm 103 on a surgical microscope stand. In this way, a physician performing a surgical procedure is enabled to position the ophthalmic surgical microscope 100 in a desired viewing position relative to the eye 104 of a patient. The ophthalmic surgical microscope 100 is configured as a stereomicroscope and has a binocular tube 105 via which the operating physician can view an operating area magnified via the zoom system and the microscope main objective system 102.

The patient eye 104 is a spatially extended organ having a vitreous body 106 which is arranged between the anterior chamber 107 with the cornea and lens and the retina 108. The spatial expanse of the vitreous body 106 is approximately 17 mm.

The spatial expanse of the vitreous body 106 therefore exceeds the depth of field of a surgical microscope which usually lies between 0.35 mm and 4 mm depending upon the adjusted magnification.

Accordingly, an operating physician performing a surgical procedure on a patient eye must readjust the surgical microscope when the surgeon wants to sharply see with the surgical microscope different sections of the eye which lie spatially apart.

In the relaxed state in this case, the eye is adapted to infinity, the cornea and lens of a healthy patient eye ensure that a parallel bundle of light rays incident on the eye is focused on the ocular fundus. In order to enable an operating physician to also sharply see regions, which lie deep in the interior of the eye, with a surgical microscope 100, the surgical microscope 100 is provided with an ophthalmoscopic magnifier 109. The ophthalmoscopic magnifier 109 has a positive refractive power. The magnifier 109 is held with a system for beam transposition and image reversion 110 on an adjustable holder 111 about the axis 112 on the surgical microscope base body 101. The holder 111 together with the ophthalmoscopic magnifier 109 and the system for beam transposition and image reversion 110 can be pivoted about the axis 112 in and out of the viewing beam path of the surgical microscope in the manner indicated by the double arrow 113. The ophthalmic surgical microscope 100 has an autofocusing system which is controlled by an autofocusing system control unit 120. The configuration and operation of the autofocusing system is explained in greater detail with respect to FIGS. 2 to 5.

Figure 2:
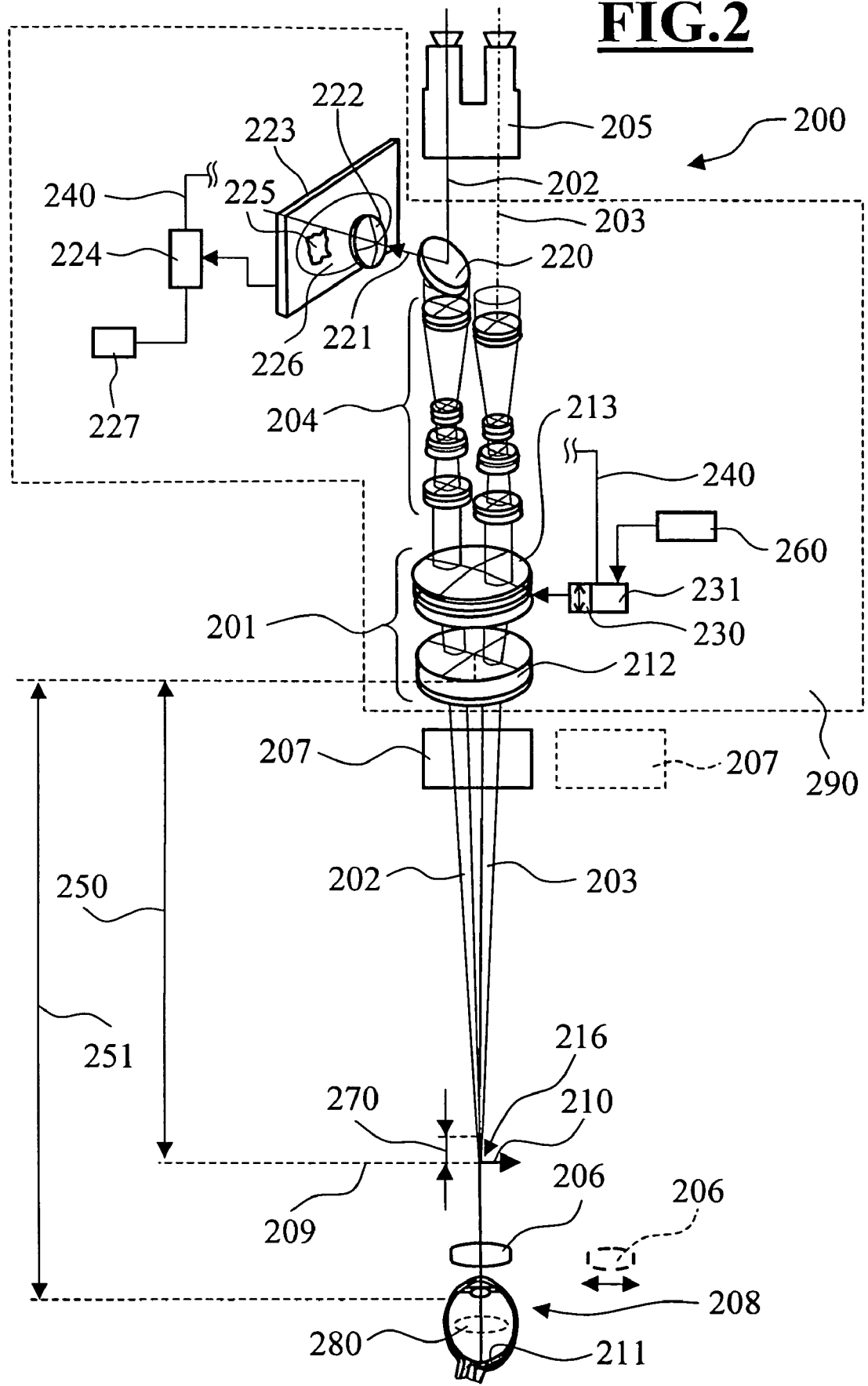
FIG. 2 is a perspective function diagram of an autofocus system in the ophthalmic surgical microscope of FIG. 1 for an optical viewing beam path including an ophthalmoscopic magnifier and an optical viewing beam path without the ophthalmoscopic magnifier.

FIG. 2 schematically shows the configuration of the ophthalmic surgical microscope 100 of FIG. 1 as a microscopic arrangement 200. In the ophthalmic surgical microscope, the stereoscopic viewing beam paths (202, 203) pass through the microscope main objective system 201 and these viewing beam paths are guided to a binocular tube 205 via a zoom system 204. The microscopic arrangement 200 further includes an ophthalmoscopic magnifier 206 and a system for beam transposition and image reversion 207 which can be pivoted in and out of the viewing beam paths (202, 203). A corresponding system for beam transposition and image reversion 207 is described, for example, in United States patent application publication US 2003/0165012 A1.

It is noted that it is also possible to provide a corresponding system for beam transposition and image reversion on the side of the microscope main objective, which faces away from the object, or to provide this system for beam transposition and image reversion at the output end of the zoom system 204. Also, a system for beam transposition and image reversion can be digitally configured basically while utilizing suitable image sensors and a corresponding image generating unit.

In FIG. 2, the viewing beam paths (202, 203) are shown for investigating the eye 208 of a patient when the ophthalmoscopic magnifier 206 and the system for beam transposition and image reversion 207 are pivoted in front of the microscope main objective system 201.

The ophthalmoscopic magnifier 206 generates an intermediate image 210 of the ocular fundus 211 of the patient's eye 208 in an intermediate image plane 207. The intermediate image 210 can be viewed magnified as well as image correctly and laterally correctly via the binocular tube 205 because of a system for beam transposition and image reversion 207 arranged in the optical viewing beam path via the zoom system 204. The intermediate image 210 is laterally inverted and image inverted with reference to the ocular fundus.

An autofocusing system 290 is provided in the microscopic arrangement 200. The autofocusing system 290 includes a partially transmissive viewing beam outcoupling element 220 mounted at the output end of the zoom system 204. The viewing beam outcoupling element 220 partially couples out the viewing beam path 202 with a beam path 221 and guides this beam path via a lens element 222 to an image sensor 223. An evaluation unit 224 is assigned to the image sensor 223. In the evaluation unit 224, the contrast is evaluated in an autofocus window which corresponds to a part region 225 of the image 226 detected by the image sensor 223. The autofocus window is selectable by the surgeon and is made visible in the binocular tube 205 to a surgeon via a data reflect-in unit (not shown). An image section selection unit 227 is connected to the evaluation unit 224. Via this image section selection unit 227, the surgeon can select the part region 225 of the image 226 detected by the image sensor 223 and evaluate the contrast thereof with the evaluation unit 224.

The microscope main objective system 201 has a fixed lens group 212 and a moveably mounted lens group 213. A drive 230 having a control unit 231 is assigned to the moveably mounted lens group 213. This control unit 231 is connected via a control line 240 to the evaluation unit 224 of the autofocusing system 290.

The intercept distance 250 is the distance of the object-end surface of the lens group 212 from the focal plane 209 in which the intersect point 216 of the viewing beam paths (202, 203) lie. The intercept distance 250 of the microscope main objective system 201 can be changed by displacing the moveably mounted lens group 213 via drive 230. The intercept distance of the microscope main objective system 201 is identified by reference numeral 251 when the ophthalmoscopic magnifier 206 and the system for beam transposition and image reversion 207 are pivoted out of the viewing beam paths (202, 203).

The autofocusing system 290 has a focus offset adjusting unit 260 which enables an operator to set a defined offset 270 of an intercept distance 250 of the microscope main objective system 201 from an intercept distance of the microscope main objective system 201 corresponding to a focusing state of the surgical microscope.

When activating the autofocusing system 290, the intercept distance of the main objective system 201 is first controlled to a value for the maximum image contrast in the selected autofocus in dependence upon the contrast signal detected by the image sensor 223. For the adjusting situation of the microscopic arrangement 200 shown in FIG. 2, the main objective system 201 therefore automatically so adjusts that the intercept distance 250 corresponds to the position of the real intermediate image 210 of the ocular fundus of the patient eye 208. The real intermediate image 210 is generated by the ophthalmoscopic magnifier 206. In the next step, the intercept distance 251 of the system is adjusted corresponding to the value pregiven by the focus offset adjusting unit 260. In this way, an operator can automatically sharply see the region in the plane 280 in the patient eye 208 by activating the autofocus system.

Figure 3:
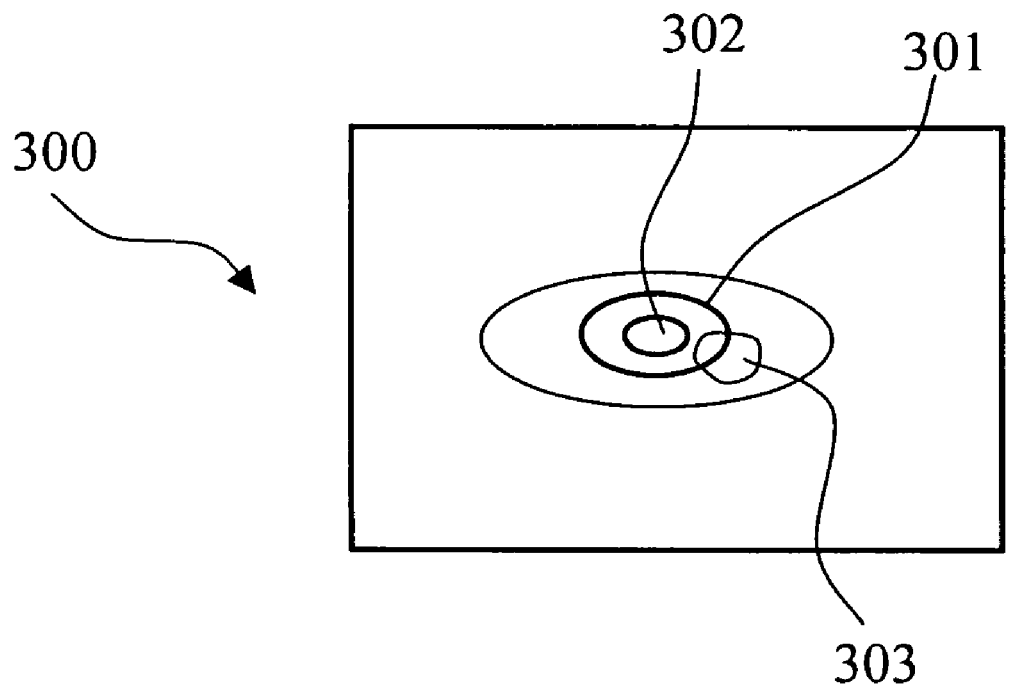
FIGS. 3 and 4 show viewing images for an operator of the ophthalmic surgical microscope of FIG. 1 while investigating a human eye.

FIG. 3 shows the viewing image 300 of a human eye which is seen by an operator in the binocular tube 205 of the microscopic arrangement 200 in FIG. 2 when the distance between the cornea of an investigated patient eye from the front lens of the microscope main objective system corresponds approximately to the intercept distance of the microscope main objective system. The ophthalmoscopic magnifier and the system for beam transposition and image reversion are pivoted out of the viewing beam paths. In viewing image 300, a surgeon can recognize, as structure, the iris 301 lying below the cornea. In order to be able to sharply see structures in the anterior region of the eye of the patient, the surgeon activates the autofocusing system 290 in the microscope system 200 of FIG. 2 and, in a first step, selects an image region 303 of which the surgeon knows that this region is based on a biological structure having good contrast. A part region is then selected from the image region 303 with the image section selection unit 227 of the microscopic arrangement 200 of FIG. 2.

Figure 4:
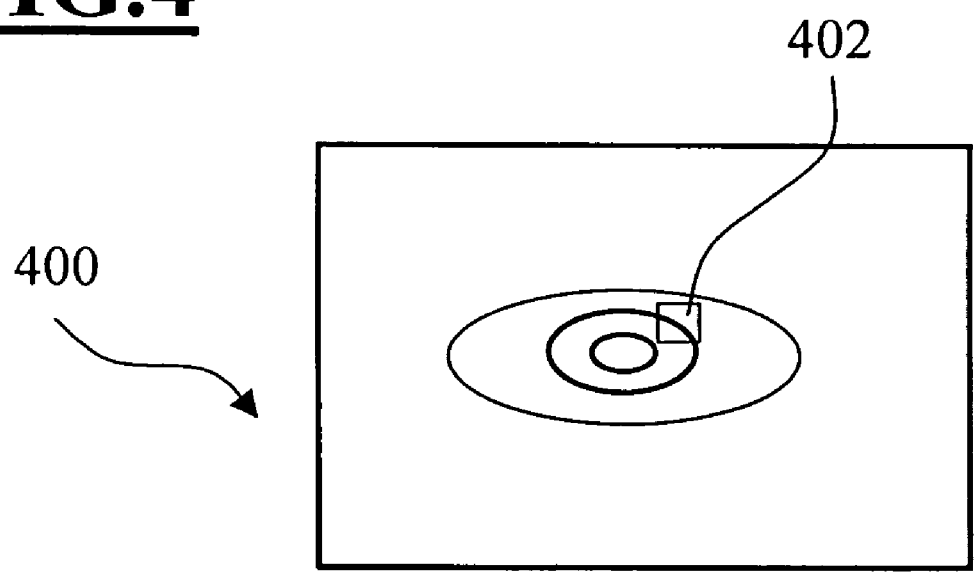

FIG. 4 shows the viewing image 400 of a human eye in the microscope arrangement 200 of FIG. 2 wherein the part region 402 is selected which includes a section of the iris of the patient eye.

When the surgeon activates the autofocusing system 290 of FIG. 2, the intercept distance of the microscope main objective system 201 of FIG. 2 is so adjusted by means of the signal of the selection unit 227 that the selected image region 225 is imaged on the image sensor 223 with maximum contrast. This corresponds to a state wherein the surgical microscope is focused exactly on the iris of the patient eye. When this state is reached, then the intercept distance of the microscope main objective system 201 is defocused in a defined manner in correspondence to the value pregiven by the focus offset adjusting unit.

In this way, it is possible for a surgeon, in the surgical microscope having an autofocusing system, to input that the surgical microscope automatically adjusts sharply to a plane which is at a pregiven distance from the iris of the human eye.

The surgeon can proceed correspondingly to focus the surgical microscope onto the ocular fundus 302 in FIG. 3 with the ophthalmoscopic magnifier pivoted into the viewing beam path. Then, the system can be sharply set also to planes which are at a pregiven distance from the ocular fundus of the patient's eye.

Figure 5:
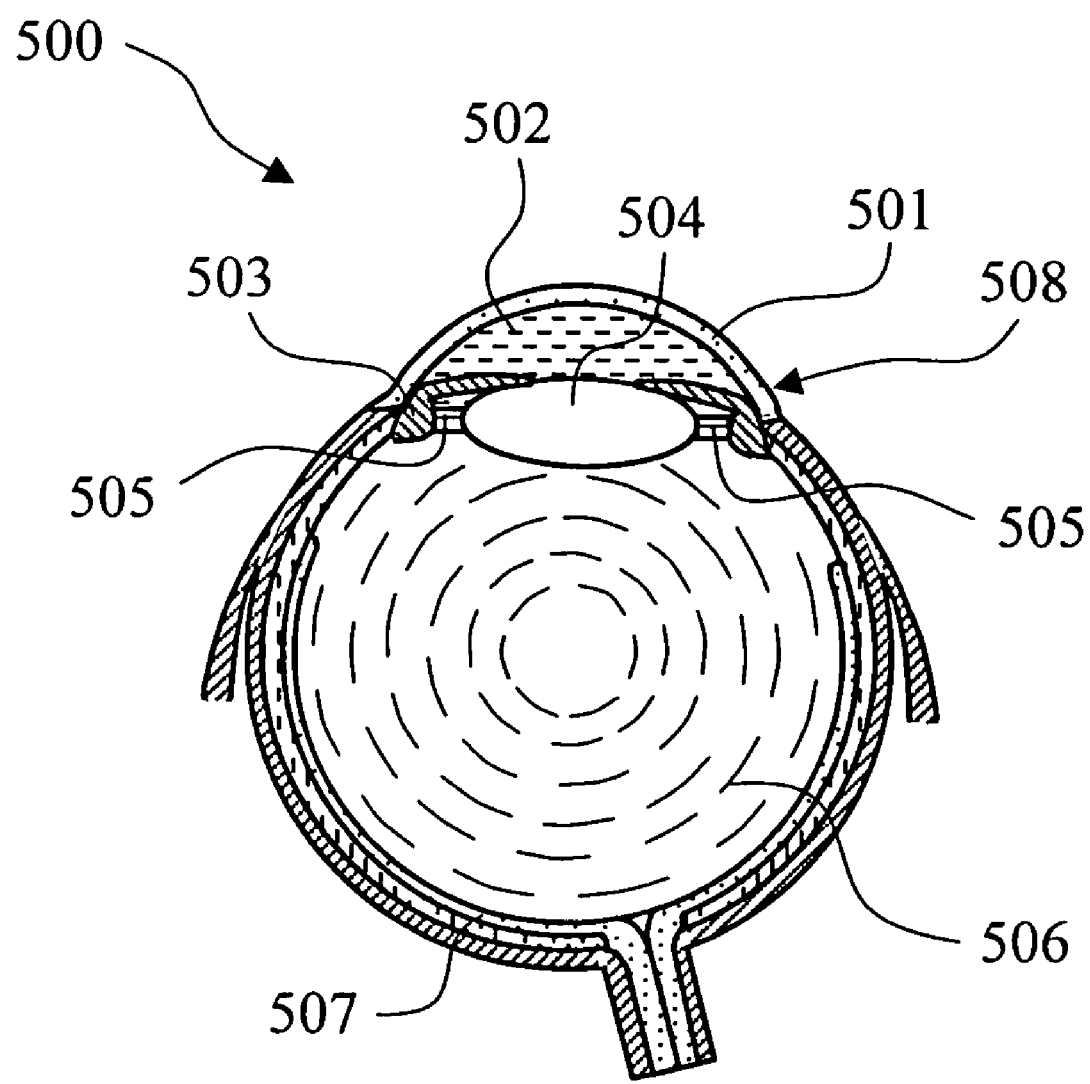
FIG. 5 is a section view of the human eye with respect to which the work with the autofocusing system in ophthalmic surgical microscopes will be explained.

FIG. 5 shows a section view of a human eye 500. The human eye 500 has a cornea 501 which surrounds the so-called anterior chamber 502 with this chamber being delimited by iris 503 and lens body 504. The lens body 504 is held in a vitreous body 506 via the zonular fibers 505. The vitreous body 506 is filled with a jelly-like mass and the retina 507 is on the rear thereof.

With the surgical microscope described with respect to FIGS. 1 to 4, it is possible to displace the focal plane in a defined manner by a specific amount forward or rearward of an object plane in which the image information is present which can be applied for focusing of the surgical microscope.

For surgery on the retina such as for the so-called membrane peeling, it is purposeful that the focus plane of the surgical microscope does not lie precisely at the retina 507, rather, that the focal plane is at a specific distance from the retina in the vitreous body. In membrane peeling, membranes are removed from the retina and these membranes are, as a rule, several tenths of a millimeter in front of the surface of the retina 507 facing toward the vitreous body 506. Such a surgery must be carried out while utilizing a contact glass or an ophthalmoscopic magnifier. Because of the refractive power of the cornea 501 and the lens body 504, the human eye 500 can only be imaged sharply in a region of a few millimeters behind the lens 504 without these optical elements. Especially with respect to membrane peeling, it is, however, important that the surgeon sharply sees the ocular fundus and the structures which extend from there into the vitreous body because the surgeon undertakes these surgical interventions with fine pincers, scissors or vitrectonomy pieces.

Also for surgery in the forward eye section, it is practical when the focal plane of the surgical microscope is not coincident with the plane wherein structures are disposed which make possible a focusing of the surgical microscope. If the lens body 504 is removed in cataract surgery, it is practical to so position the focus plane of the microscope main objective that the surgical microscope need not be refocused during removal of the lens. As a rule, cataract surgery begins with a small puncture in the limbus region 508 of the cornea 501 through which surgical instruments are then introduced into the forward section of the eye. Thereafter, the so-called "capsulorhexis" is carried out. A circularly-shaped opening is made in the forward capsule of the lens 504 of the eye of the patient. This region lies virtually in the same plane as the iris 503 of the eye of the patient. The eye lens 504 usually has a thickness of approximately 3.5 mm to 5.5 mm. When drawing off the eye lens 504 by suction, the surgeon, however, operates with a phakoprobe in a plane which is offset toward the vitreous body 506 by a few millimeters referred to the iris 503 of the eye of the patient. In order to work here without refocusing the surgical microscope, it is practical to utilize the depth of field of the instrument and, ab initio, to adjust the focal plane of the surgical microscope with an offset to the plane in which the iris of the eye of the patient is disposed. The iris has a structure the information of which can be applied for the focusing of the surgical microscope.

Figure 6:
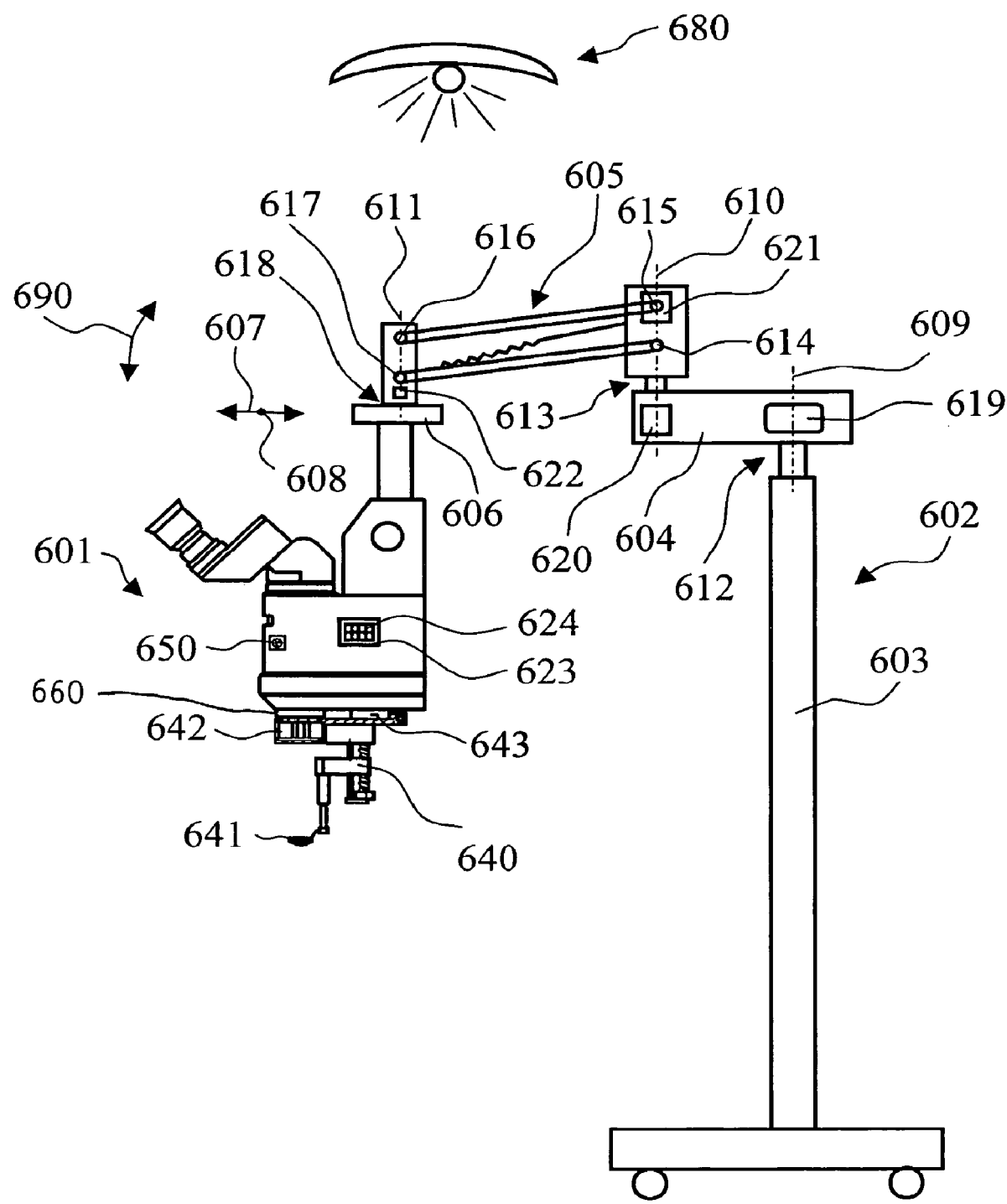
FIG. 6 shows the ophthalmic surgical microscope of FIG. 1 mounted on a surgical microscope stand in an operating room.

FIG. 6 shows the ophthalmic surgical microscope 601 of FIG. 1 as a microscope arrangement on a stand 602 arranged in an operating room having surgical illumination 680. The stand 602 includes a stand column 603 having a first carrier arm 604 and a second carrier arm 605 which is configured as an articulated parallelogram. The ophthalmic surgical microscope 601 is held with a displacer unit 606 on a forward end of the second carrier arm 605. The displacer unit 606 makes possible a lateral movement in the direction indicated by arrow 607 and in a direction perpendicular thereto which is indicated by reference numeral 608. The first carrier arm 604 and the second carrier arm 605 of the ophthalmic surgical microscope 601 can be rotated about the stand axes (609, 610 and 611). The second carrier arm 605 is arranged on the first carrier arm 604 to be pivotable in the direction indicated by the double arrow 690. The stand has rotational joints (612, 613, 614, 615, 616, 617 and 618). Controllable magnetic brakes (619, 620, 621, 622) are assigned to the rotational joints (612, 613, 615 and 618) and these magnetic brakes can be opened and closed. The surgical microscope stand cannot be moved when the magnetic brakes are closed.

The surgical microscope 601 has a control unit 623 which enables the operator to do the following by pressing a key: trigger the autofocusing system in the surgical microscope; open and lock the magnetic brakes 619 to 622; and, to motorically move the surgical microscope 601 in the directions indicated by reference numerals 607 and 608. In addition, the control unit 623 enables the operator to set a specific focus offset when the autofocusing system, when activated, adjusts an intercept distance with a specific offset to the plane or intermediate image plane to which the surgical microscope can be automatically focused.

The surgical microscope 601 is furthermore so designed that, when the autofocusing system is deactivated, the microscope main objective system 660 is manually controlled motorically focused as an objective arrangement by means of the control unit 623. Alternatively, or in addition, it can be provided that the microscope main objective system 660 is mechanically adjusted by means of a suitable unit.

An autofocusing system activation state can be set on the control unit 623 in which an electric switch 643 is coupled to the pivotable receptacle 640 of the ophthalmoscopic magnifier 641 and the system for beam transposition and image reversion 642. The switch 643 is preferably configured as a microswitch. In addition, the electric switch 643 is connected to the autofocusing system in the surgical microscope in such a manner that the surgical microscope 601 is automatically focused onto a plane in the eye of a patient when the ophthalmoscopic magnifier 641 is pivoted in and out.

In this autofocusing system activation state, it can be provided that, with a pivoting of the ophthalmoscopic magnifier into the viewing beam path, an ocular fundus illumination 650 of the ophthalmic surgical microscope 601 is triggered which is again switched off with the pivoting of the ophthalmoscopic magnifier 641 out of the viewing beam path.

In addition, it is possible with the surgical microscope 601 to adjust a specific focus offset of the microscope main objective system 660 by means of the control unit 623. This focus offset is automatically adjusted after a corresponding input of a value during activation of a key field 624 of the control unit 623.

With the control unit 623, an operating mode of the surgical microscope can be set wherein a coupling of the electric switch 643 to the automatic focus offset is provided. If the surgical microscope is first automatically or manually focused on the iris of an eye of a patient (whereby the pivotable receptacle 640 with ophthalmoscopic magnifier 641 and the system for beam transposition and image reversion are pivoted out of the optical viewing beam path), then the pivoting in of the ophthalmoscopic magnifier 641 and the system for beam transposition and image reversion 642 causes a switching signal of the electric switch 643. This switching signal triggers a shift of the focus plane of the microscope main objective 660 in a direction of the objective front surface in order to shift this focus plane so that the viewing beam paths of the surgical microscope 601 (which then also pass through the system for beam transposition and image reversion 642) intersect in the plane of the intermediate image of the ocular fundus of the patient eye which is generated by the ophthalmoscopic magnifier 641. The plane of the intermediate image usually is disposed approximately 1 cm from the main plane of this optical element between this optical element and the microscope main objective 660.

In the surgical microscope 601, a reverse operating mode is also provided which is correspondingly adjustable by means of the control unit 623. If the surgical microscope is first manually or automatically sharply focused on the image of an ocular fundus generated with the ophthalmoscopic magnifier 641 with the ophthalmoscopic magnifier and system for beam transposition and image reversion pivoted into the optical viewing beam path, then the automatic actuation of the electric switch 643 (when the ophthalmoscopic magnifier 641 and the system for beam transposition and image reversion 642 on the holder 640 are pivoted out of the optical viewing beam path) causes an offset of the focus plane of the microscope main objective 660 in the direction of the patient eye by approximately 2 cm to 5 cm so that the focus plane then lies in the region of a lens of the patient eye.

Alternatively, or in addition, it is also possible to control the illumination 680 of the operating room by means of the electric switch 643 in the manner that the light in the operating room is dimmed when pivoting the ophthalmoscopic magnifier 641 into the viewing beam path. Optionally or alternatively, by means of the electric switch 643, an image inverter can be activated and/or a digital image inversion of a video camera, which is assigned to the surgical microscope 601, is triggered.

Figure 7:
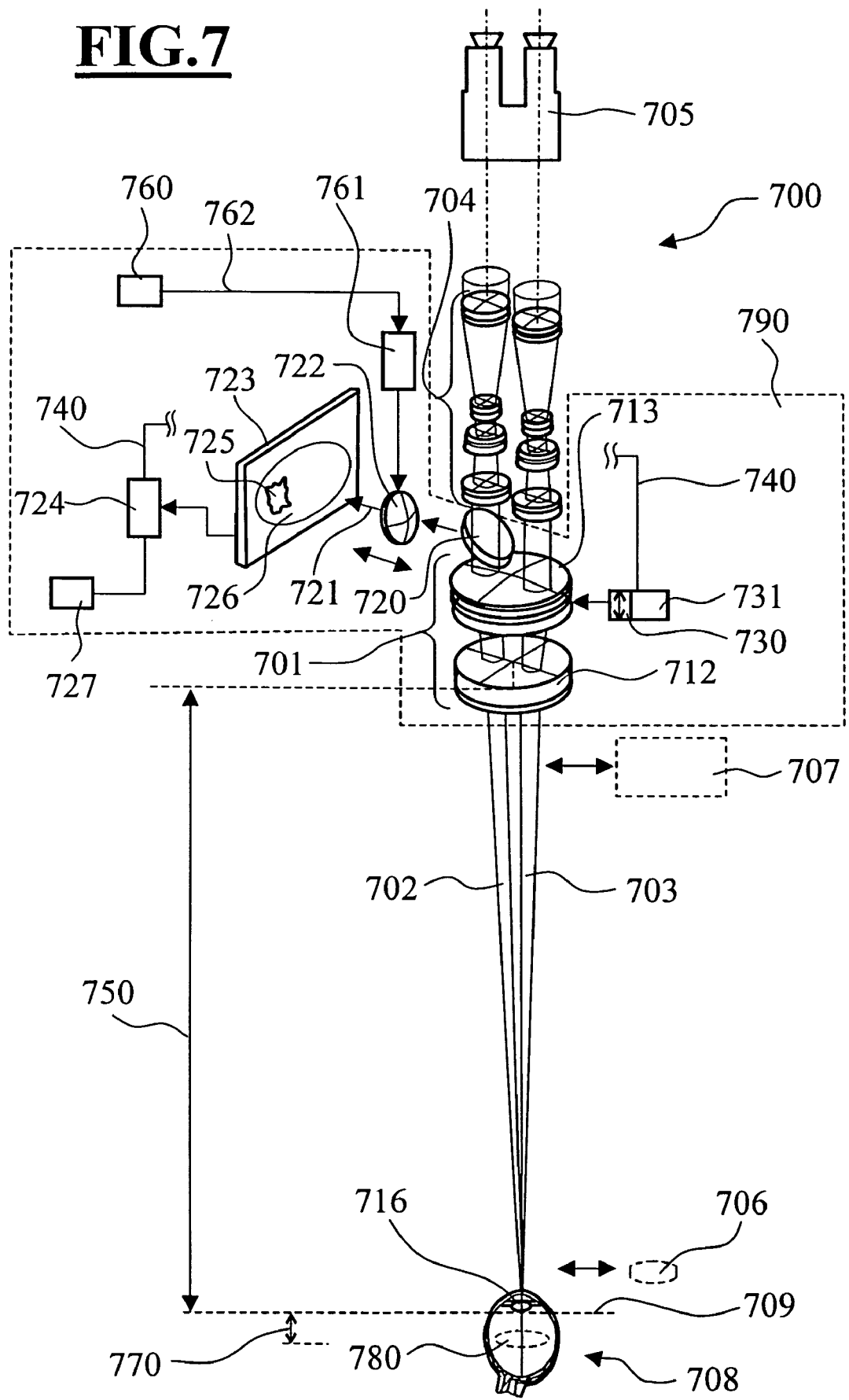
FIG. 7 is a modified embodiment of a microscopic arrangement including an autofocus system for an ophthalmic surgical microscope; and, FIG. 8 is a further modified embodiment of a microscopic arrangement having an autofocus system which is suitable especially for a neurosurgical microscope.

FIG. 7 shows a microscope arrangement 700 modified in comparison to FIG. 2. The microscope arrangement 700 has an autofocusing system 790 which is likewise suitable especially for use in an ophthalmoscopic surgical microscope. The microscope arrangement 700 has a microscope main objective system 701 through which stereoscopic viewing beam paths (702, 703) pass and which are conducted via a zoom system 704 to a binocular tube 705. The microscope arrangement 700 further includes an ophthalmoscopic magnifier 706 and a system for beam transposition and image reversion 707 which can be pivoted in and out of the viewing beam paths (702, 703) as in the microscope arrangement 200 of FIG. 2. The microscope arrangement 700 is shown in a state wherein the ophthalmoscopic magnifier 706 and the image reversion system are outside of the viewing beam paths (702, 703).

The microscope arrangement 700 has an autofocusing system 790 which has a partially permeable viewing beam outcoupling element 720. As a departure from the microscope system 200 of FIG. 2, this viewing beam outcoupling element 720 is mounted between the microscope main objective system 701 and the zoom system 704. It is, however, noted that also an arrangement of this viewing beam outcoupling element as in the microscope arrangement 200 of FIG. 2 would be possible.

The viewing beam outcoupling element 720 couples the viewing beam path 702 partially laterally out with a beam path 721 and leads this beam path to an image sensor 723 via a lens element 722. An evaluation unit 724 is assigned to the image sensor 723. In the evaluation unit, the contrast in an autofocus window, which is selectable by an operator, is evaluated. The autofocus window corresponds to a part region 725 of the image 726 detected by the image sensor 723. The autofocus window is made visible in the binocular tube 705 to an operator via a data in-reflecting unit (not shown). The operator can select the part region 725 of the image 726 detected by the image sensor 723 via an image section selection unit 727 connected to the evaluation unit 724. The contrast of the image 726 is evaluated with the evaluation unit 724.

The microscope main objective system 701 has a fixed lens group 712 and a moveably mounted lens group 713. A drive 730 having a control unit 731 is assigned to the moveably mounted lens group 713. As in the microscope arrangement 200 of FIG. 2, this control unit is connected via a control line 740 to the evaluation unit 724 of the autofocusing system 790.

The intercept distance 750 of the microscope main objective system 701 is the distance of the object side surface of the lens group 712 from the intersect point 716 of the viewing beam paths (702, 703). The intercept distance 750 can be changed by displacing the moveably mounted lens group 713 by means of the drive 730.

The autofocus system 790 has a focus offset adjusting unit 760 which makes it possible for an operator to adjust a defined offset 770 of an intercept distance 750 of the microscope main objective system 701 from an object plane 709 with maximum contrast. The focus offset adjusting unit 760 is connected a via signal line 762 drive unit 761 for the lens element 722. The lens element 722 is adjusted in the beam path 721 in correspondence to the pregiven offset.

When activating the autofocus system 790, the intercept distance of the main objective system 701 is controlled to a value for the maximum image contrast on the image sensor 723 in dependence upon the contrast signal detected via the image sensor 723. By activating the autofocus system, the surgeon sees the region 780 in the patient eye 708 which is offset to the plane which is imaged onto the image sensor 723 for the purpose of contrast determination.

Figure 8:
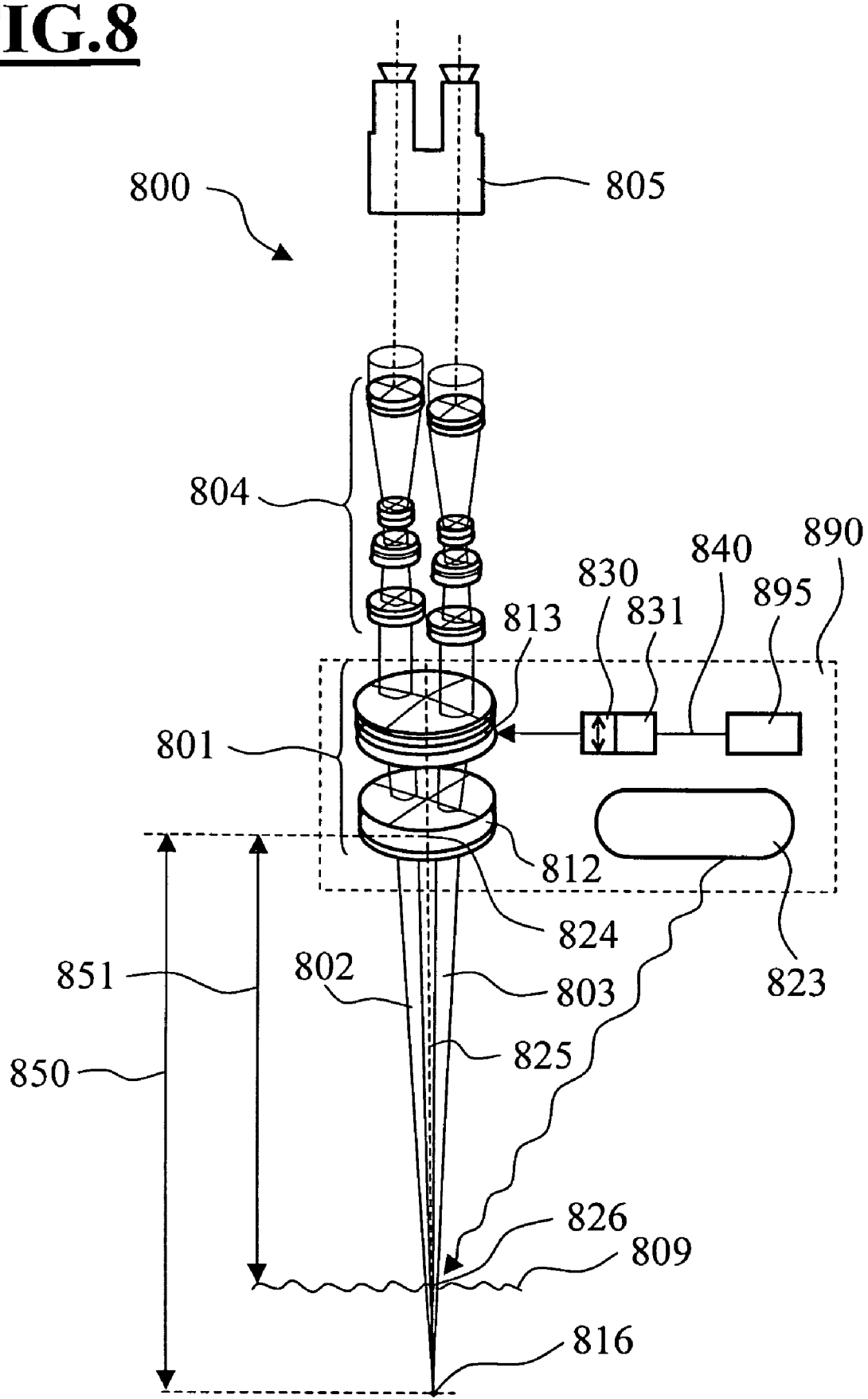

FIG. 8 shows a microscope arrangement 800 having an autofocus system 890 which is especially suited for use in a surgical microscope designed for neurosurgery. The microscope arrangement has a main objective system 801 through which stereoscopic viewing beam paths (802, 803) pass. The viewing beam paths (802, 803) are conducted via a zoom system 804 to a binocular tube 805 through which a surgeon can view an object region 809.

The microscope main objective system 801 has a fixed lens group 812 and a moveably mounted lens group 813. A drive 830 having a control unit 831 is assigned to the moveably mounted lens group 813. The control unit 831 is connected via a control line 840 to the evaluating unit 895 of the autofocus system 890. The intercept distance 850 of the microscope main objective system 801 is the distance of the object side surface of the lens group 812 from the intersect point 816 of the viewing beam paths (802, 803). The intercept distance 850 can be changed by displacing the moveably mounted lens group 813 by means of the drive 830.

The autofocus system 890 furthermore includes a unit 823 for determining the focusing state of the microscope main objective 801 with reference to the object region 809. The unit 823 is for specifying the focusing state and is configured, for example, as in the microscope arrangement described with respect to FIG. 1 of U.S. patent application publication US 2004/0090667 A1. In this unit, the offset data of the scattered light from two analysis light beams, which are conducted through the microscope main objective system, are applied as input quantities for a control loop which so adjusts the microscope main objective system that the latter automatically focuses onto the object region. As described with respect to FIG. 5 of U.S. patent application publication U.S.2004/0090667 A1, it is also, however, possible to evaluate the pattern of the stray light of an analysis light beam which is conducted to the object region in order to thereby detect a focusing state of the microscope main objective system.

When activating the autofocus system 890, and in dependence upon the distance signal detected by the unit 823, the intercept distance of the main objective system 801 is set to a value which corresponds to the position of the object region modified by the adjusted offset. In this way, a surgeon can automatically sharply see a region lying offset to the surface of the object region by activating the autofocus system 890.

Alternatively, it is possible to configure the unit 823 as a distance measuring unit which can determine the distance 851 of the front surface of the microscope main objective system 801 from the object region 809. Then, with the unit 823, the distance 851 between the intercept point 824 of the optical axis 825 of the microscope main objective system 801 can be determined from the front surface of this system and the intercept point 826 of the optical axis 825 with the object region 809. This distance measurement can, for example, take place on an image sensor by determining the offset of scatter light of an analysis light beam which is conducted through the microscope main objective system. Alternatively, it is, for example, possible to carry out the distance measurement as a running time measurement of a light pulse or an ultrasonic signal.

In this case, via the autofocus system 890, the intercept distance of the main objective system 801 is so moved in dependence upon the distance signal detected via the unit 823 that this corresponds to the position of the object region modified by the pregiven offset. In this way, it is likewise achieved that a surgeon, by activating the autofocus system 890, automatically sharply sees a region lying offset to the surface of the object region.

It is understood that the foregoing description is that of the preferred embodiments of the invention and that various changes and modifications may be made thereto without departing from the spirit and scope of the invention as defined in the appended claims.

What is claimed is:

1. An ophthalmic surgical microscope for microsurgery for viewing an object or an intermediate image generated by the object, the ophthalmic surgical microscope defining a viewing beam path and comprising:
    an objective arrangement defining a focal intercept and being focusable to vary said focal intercept so as to intersect at an intercept point on an object plane or at an intermediate image thereof;
    an autofocusing system having a component assembly for detecting a focusing state of said objective arrangement and for outputting a focusing actuating signal for said objective arrangement;
    a focus offset adjusting unit assigned to said autofocusing system for outputting a focus offset signal to adjust said objective arrangement by a predetermined focus offset starting from a first focusing state wherein said objective arrangement is focused on a first object plane to a second focusing state wherein said objective arrangement is focused onto a second object plane;
    an ophthalmoscopic magnifier; and,
    means for selectively moving said ophthalmoscopic magnifier between a first position whereat said ophthalmoscopic magnifier is disposed in said viewing beam path and a second position whereat said ophthalmoscopic magnifier is outside of said viewing beam path.

2. The ophthalmic surgical microscope of claim 1, wherein said focus offset adjusting unit includes an input unit adapted to permit an operator to select a desired value for an offset of the focus of said objective arrangement from a focusing state which said focus offset adjusting unit sets.

3. The ophthalmic surgical microscope of claim 1, further comprising means for determining an image contrast assigned to said component assembly.

4. The ophthalmic surgical microscope of claim 3, further comprising selection means for selecting a zone of an image; and, means for determining the contrast of said zone of said image.

5. An ophthalmic surgical microscope for microsurgery for viewing an object or an intermediate image generated by the object, the ophthalmic surgical microscope defining a viewing beam path and comprising:
    an objective arrangement defining a focal intercept and being focusable to vary said focal intercept so as to intersect at an intercept point on an object plane or at an intermediate image thereof;

an autofocusing system having a component assembly for detecting a focusing state of said objective arrangement and for outputting a focusing actuating signal for said objective arrangement;

a focus offset adjusting unit assigned to said autofocusing system for outputting a focus offset signal to adjust said objective arrangement by a predetermined focus offset starting from a first focusing state wherein said objective arrangement is focused on a first object plane to a second focusing state wherein said objective arrangement is focused onto a second object plane;

an ophthalmoscopic magnifier;

means for selectively moving said ophthalmoscopic magnifier between a first position whereat said ophthalmoscopic magnifier is disposed in said viewing beam path and a second position whereat said ophthalmoscopic magnifier is outside of said viewing beam path; and, switching means for activating said autofocusing system when said ophthalmoscopic magnifier is positioned in said first position.

6. The ophthalmic surgical microscope of claim 5, wherein said switching means is coupled to at least one of the following:

means for controlling an illuminating unit of said ophthalmic surgical microscope;

means for controlling an illuminating unit of an operating room;

means for arranging an image reversion system in said viewing beam path of said ophthalmic surgical microscope; and, means for controlling a stand magnetic brake.

7. The ophthalmic surgical microscope of claim 6, wherein said viewing beam path is a stereoscopic viewing beam path.

8. An ophthalmic surgical microscope for microsurgery for viewing an object or an intermediate image generated by the object, the ophthalmic surgical microscope defining a viewing beam path and comprising:

an objective arrangement defining a focal intercept and being focusable to vary said focal intercept so as to intersect at an intercept point on an object plane or at an intermediate image thereof;

an autofocusing system having a component assembly for detecting a focusing state of said objective arrangement and for outputting a focusing actuating signal for said objective arrangement;

a focus offset adjusting unit assigned to said autofocusing system for outputting a focus offset signal to adjust said objective arrangement by a predetermined focus offset starting from a first focusing state wherein said objective arrangement is focused on a first object plane to a second focusing state wherein said objective arrangement is focused onto a second object plane;

an ophthalmoscopic magnifier;

means for selectively moving said ophthalmoscopic magnifier between a first position whereat said ophthalmoscopic magnifier is disposed in said viewing beam path and a second position whereat said ophthalmoscopic magnifier is outside of said viewing beam path; and, switching means for activating said autofocusing system when said ophthalmoscopic magnifier is positioned in said second position.

9. The ophthalmic surgical microscope of claim 8, wherein said switching means is coupled to at least one of the following:

means for controlling an illuminating unit of said ophthalmic surgical microscope;

means for controlling an illuminating unit of an operating room;

means for arranging an image reversion system in said viewing beam path of said ophthalmic surgical microscope; and.

means for controlling a stand magnetic brake.

10. The ophthalmic surgical microscope of claim 9, wherein said viewing beam path is a stereoscopic viewing beam path.

* * * * *

UNITED STATES PATENT AND TRADEMARK OFFICE
CERTIFICATE OF CORRECTION

| | | |
|---|---|---|
| PATENT NO. | : 7,554,723 B2 | Page 1 of 1 |
| APPLICATION NO. | : 11/372209 | |
| DATED | : June 30, 2009 | |
| INVENTOR(S) | : Gerhard Moeller, Peter Reimer and Peter Andrews | |

It is certified that error appears in the above-identified patent and that said Letters Patent is hereby corrected as shown below:

Column 6:
Line 11: delete "207" and substitute -- 209 -- therefor.

Column 11:
Line 6: insert -- to -- after "762".

Signed and Sealed this

Fourth Day of August, 2009

JOHN DOLL
*Acting Director of the United States Patent and Trademark Office*